US007604394B2

(12) United States Patent
Krishnamoorthy et al.

(10) Patent No.: US 7,604,394 B2
(45) Date of Patent: Oct. 20, 2009

(54) SELF-CLEANING AND MIXING MICROFLUIDIC ELEMENTS

(75) Inventors: Sivaramakrishnan Krishnamoorthy, Madison, AL (US); Jianjun Feng, Cincinnati, OH (US)

(73) Assignee: CFD Research Corporation, Huntsville, AL (US)

(*) Notice: Subject to any disclaimer, the term of this patent is extended or adjusted under 35 U.S.C. 154(b) by 467 days.

(21) Appl. No.: 11/516,358

(22) Filed: Sep. 6, 2006

(65) Prior Publication Data

US 2007/0209940 A1 Sep. 13, 2007

Related U.S. Application Data

(63) Continuation-in-part of application No. 10/307,907, filed on Dec. 2, 2002, now Pat. No. 7,189,578.

(51) Int. Cl.

| | |
|---|---|
| ***B01F 13/00*** | (2006.01) |
| ***H02K 44/00*** | (2006.01) |
| ***C12Q 1/68*** | (2006.01) |
| ***B03C 5/02*** | (2006.01) |

(52) U.S. Cl. .......................... 366/341; 417/50; 422/50; 204/547

(58) Field of Classification Search ...................... None
See application file for complete search history.

(56) References Cited

U.S. PATENT DOCUMENTS

| | | | | |
|---|---|---|---|---|
| 6,902,313 | B2 * | 6/2005 | Ho et al. | 366/108 |
| 7,189,578 | B1 * | 3/2007 | Feng et al. | 422/68.1 |
| 2003/0086333 | A1 * | 5/2003 | Tsouris et al. | 366/173.1 |
| 2003/0169637 | A1 * | 9/2003 | Lee et al. | 366/165.2 |
| 2004/0156725 | A1 * | 8/2004 | Bau | 417/48 |
| 2004/0231990 | A1 * | 11/2004 | Aubry et al. | 204/547 |
| 2004/0256230 | A1 * | 12/2004 | Yager et al. | 204/450 |
| 2005/0040035 | A1 * | 2/2005 | Mpholo et al. | 204/288 |
| 2008/0000772 | A1 * | 1/2008 | Bazant et al. | 204/450 |
| 2008/0047833 | A1 * | 2/2008 | Hirahara et al. | 204/450 |

* cited by examiner

*Primary Examiner*—Jill Warden
*Assistant Examiner*—Timothy G Kingan
(74) *Attorney, Agent, or Firm*—Tomas H. F. Friend

(57) ABSTRACT

Apparatus and methods are disclosed for mixing and self-cleaning elements in microfluidic systems based on electrothermally induced fluid flow. The apparatus and methods provide for the control of fluid flow in and between components in a microfluidic system to cause the removal of unwanted liquids and particulates or mixing of liquids. The geometry and position of electrodes is adjusted to generate a temperature gradient in the liquid, thereby causing a non-uniform distribution of dielectric properties within the liquid. The dielectric non-uniformity produces a body force and flow in the solution, which is controlled by element and electrode geometries, electrode placement, and the frequency and waveform of the applied voltage.

3 Claims, 16 Drawing Sheets

(a)

(b)

(a)

(b)

(a)

(b)

(a)

(b)

SELF-CLEANING AND MIXING MICROFLUIDIC ELEMENTS

CROSS-REFERENCE TO RELATED APPLICATIONS

This Application is a Continuation In Part of application Ser. No. 10/307,907, filed 02 Dec. 2002 now U.S. Pat. No. 7,189,578.

STATEMENT REGARDING FEDERALLY SPONSORED RESEARCH OR DEVELOPMENT

The U.S. Government may have certain rights in this invention pursuant to SBIR Contract Number W81XWH06C0067 awarded by the United States Army

INCORPORATED-BY-REFERENCE OF MATERIAL SUBMITTED ON A COMPACT DISC

Not Applicable

BACKGROUND OF THE INVENTION

1. Field of the Invention

The present invention relates generally to devices and methods used for mixing and cleaning in microfluidic systems. More particularly, this invention pertains to self-cleaning elements and mixing elements for use in microfluidic systems such as lab-on-a-chip and BIOMEMS systems.

2. Description of Related Art

Miniaturized bioanalytical, lab-on-a-chip, integrated microfluidic and Bio-Micro Electro Mechanical Systems ("BioMEMS") (hereafter collectively referred as microdevices) are used to perform various functions such as a simple mixing of two or more analytes or liquid streams (hereafter collectively referred as samples) to a more complex biochemical assay that can include immunoassays, DNA hybridization, and general cell-molecule interactions. These devices incorporate many of the necessary components on a single platform, known as a biochip or microfluidic chip (hereafter collectively referred as microfluidic system). The term "microfluidic" is commonly used if at least one characteristic dimension of the device is in micron size. Typical biochip components known in the art include reaction chambers, pumps, micromixers, pre-concentrators, interconnects, separators, and sensors. The successful implementation of a biochemical assay using a microfluidic system is determined in terms of parameters that can include overall assay time, recovery time, sensitivity, selectivity, and accuracy.

In microdevices, samples are usually mixed as a part of an assay protocol. The time taken to accomplish this task, known as "mixing time", is determined by the diffusion coefficient (usually a very small value) of the samples, their flow speed, and residence time inside the device. This time can form a significant portion of the "overall assay time". In this regard, there is a need for methods and systems that will facilitate rapid mixing so that overall assay time may be reduced. Preferably, such devices should contain no moving parts.

A second performance parameter is the recovery time, which is defined as the time taken for the device to get ready before analyzing next set of samples. This requires cleaning of the device, including the cleaning of reaction chambers, pumps, micromixers, pre-concentrators, interconnects, separators, and sensors. Cleaning may involve the removal of unwanted liquids and particulates. The presence of a liquid or particulates used in a microfluidic device for one application may be undesirable in a subsequent application. In this aspect also, there is a similar need for systems and methods that will facilitate efficient cleaning.

Most conventional micromixing systems can be classified as either active or passive. Passive mixers use molecular diffusion of samples, and consequently take a very long time to accomplish mixing. Active mixers use externally imposed forcing mechanisms, such as a pressure pulse or an oscillatory flow, and therefore take a relatively short time to accomplish mixing. Known methods of micromixing include electroosmotic flow (electrohydrodynamic instabilities), static lamination (diffusional forces as mixing mechanism), and injection of one liquid into another liquid with microplumes.

Passive mixers do not have any moving parts, in contrast to active devices where moving parts are activated either by a pressure or by an electric field. Passive mixers use channel geometry to increase residence time. Passive micromixers are further subdivided into in-plane and out-of-plane mixers. In-plane mixers divide and mix various liquid streams in one dimension while out-of-plane mixers use three-dimensional channel geometries to enhance mixing. The simplest passive in-plane mixer is a one that merges two different liquid streams into a single channel and accomplishes mixing via molecular diffusion.

Cleaning methods that are conventionally practiced in the industry include ultrasonic cleaning and vacuum washing. Compared to mixing, the use of passive cleaning systems has received relatively little attention.

What is needed, then, are methods and systems for mixing and cleaning in microfluidic systems that use no moving parts, are easy to control, and that do not require special treatment of system surfaces.

BRIEF SUMMARY OF THE INVENTION

The present invention provides a novel method and system for inducing and controlling flow motion in a cavity or channel (hereafter referred to as a channel) or other components in a microfluidic system. A cavity can be considered as a subset of a channel where one or both ends may be closed. A channel can have any cross sectional area, including square, rectangular, trapezoidal, circular or curved (FIG. 2). The method of the invention includes positioning at least one pair of electrodes in and/or proximate to the channel. A liquid medium (hereafter referred to as a buffer) is contained inside the device. The buffer solution has at least one dielectric property that varies in response to the temperature of the solution. When an electric field, is applied to the buffer, it induces a temperature gradient in the buffer solution due to Joule heating. The applied electric field can be one of the following (a) a direct current (DC) characterized by the magnitude of applied voltage;

(b) a time varying direct current characterized by the magnitude and frequency of the applied voltage, and a having a waveform that can be sinusoidal, square, pulse, saw-toothed, or combination thereof; or (c) an alternating current (AC) characterized by magnitude and frequency of applied voltage and a waveform that can be sinusoidal, square, pulse, saw-toothed or combination thereof.

The Joule heating induces variations in the dielectric property of the buffer. The variation in the dielectric property exerts a force on the buffer and, consequently, a flow motion is observed. This motion is called an electrothermal flow. The present invention utilizes this electrothermally induced flow motion to accomplish the processes of mixing or cleaning. The magnitude, frequency and waveform of the electric field, the geometry and position of the electrodes, and geometry of the channel may be adjusted to generate a desired temperature gradient, hence desired flow, in the buffer solution.

The present invention includes a method of designing a microfluidic system to provide controllable flow motion in a buffer solution inside a channel having a fixed geometry. The designer begins by selecting either a buffer solution having a known viscosity, density and a temperature dependent dielectric property, or an electric power source having a voltage of known magnitude, frequency, and waveform. The designer then proposes a geometry for the device and a location and shape for at least one pair of electrodes to be placed in a position proximate the channel. The electrodes are connected to the electric power source. A target function that includes a desired temperature gradient inside the buffer solution and a uniformity of concentration of samples in the channel is defined. A computer simulation of the system is performed, using the selected system parameters. The simulation includes performing an optimization procedure on the target function. Following the initial simulation, the position of the electrodes can be adjusted in response to outcome. The design can further be optimized by adjusting one or more of the other system parameters, including the magnitude, frequency, and waveform of the electric voltage, and electrode shape and size, in response to performing the simulation of the system.

The use of electrothermal flows in a microfluidic system offers several advantages and benefits. First, no moving parts are involved in such systems. Also, such systems have low power requirements. For example, an electrode voltage in the range of 1 Vrms and frequency of $10^6$ Hz (of an AC field) is able to induce a flow field with maximum velocity of 100 μm/sec in microdevices. Electrothermal flow provides an ease of control. Process parameters that induce electrothermal flows are easier to measure. This allows the control of device functionality to be accomplished with ease, for example, by rearranging the electrode configuration and changing the applied electric field.

A further benefit of using electrothermal flow is that there is no need for special treatment of the channel surfaces. The flow is induced within a region of non-uniform temperature gradient and is independent of more complicated surface phenomena. This means that no complex surface modifications are needed, as required in several commercial BioMEMS devices and therefore, is relatively easy to implement.

DESCRIPTION OF THE PREFERRED EMBODIMENTS

Figure 1:
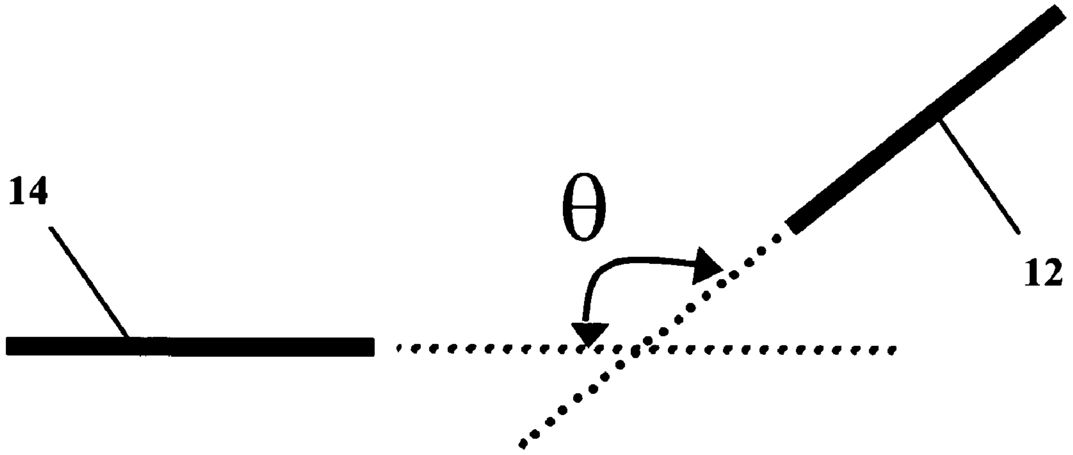
FIG. 1 is a diagram showing the geometric relationship between electrodes in an electrode pair used in the system and method of the invention to electrothermally induce flows in a microfluidic system.

Traditionally, microdevices use electric fields (AC or DC) as a source of energy to induce flow of buffer using electroosmosis, transport and separation of samples using electrophoresis, or transport of particles using dielectrophoresis. In this context, the present invention focuses on the use of an electric field to facilitate the transport and mixing of two or more analytes or liquid streams, as well as cleaning (removal of particles or analytes) of devices using electrothermally induced fluid flow.

Electrothermally Induced Fluid Flow

When an electric field is applied to a buffer, it induces a temperature gradient in the buffer solution due to Joule heating. This, in turn, induces variations (non-uniformities) in the dielectric property of the buffer. The non-uniformity in the dielectric property results in a body force being exerted on the liquid and, consequently, a flow motion is observed. The present invention utilizes this electrothermally induced flow motion to accomplish the processes of mixing or cleaning.

Dielectric materials experience an electrostatic force ($\vec{f}$) in an electric field as described by:

$$\vec{f} = \rho\vec{E} - \frac{1}{2}E^2\nabla\varepsilon + \frac{1}{2}\nabla\left[\rho_m\left(\frac{\partial\varepsilon}{\partial\rho_m}\right)_T E^2\right]$$

where $\rho_m$ is the material mass density, $\rho$ is the charge density, $\epsilon$ is the permittivity, T is the temperature, $\vec{E}$ is the applied electric field, and $\nabla$ is the gradient operator. If we assume the non-uniformity of the dielectric properties arises from their temperature dependence, we derive a first order approximation of body force exerted on the buffer as (A. Ramos, H. Morgan, N. G. Green, A. Castellanos (1998) *"AC Electrokinetics: A Review of Forces in Microelectrode Structures" Journal of Physics D*, Vol 31, pp. 2338-2353, incorporated herein by reference):

$$\vec{f} = \frac{1}{2}Re\left[\frac{\sigma\varepsilon(\alpha-\beta)}{\sigma+i\omega\varepsilon}(\nabla T\cdot\vec{E}_0)\vec{E}_0^* - \frac{1}{2}\varepsilon\alpha|\vec{E}_0|^2\nabla T\right]$$

where $$\alpha = \frac{1}{\varepsilon}\frac{\partial\varepsilon}{\partial T},\ \beta = \frac{1}{\sigma}\frac{\partial\sigma}{\partial T}$$

Here, $\omega$ is the frequency of the applied electric field, $\sigma$ is the conductivity of the media, Re represents the real part, and $\alpha$ and $\beta$ are the coefficients of variation of electrical permittivity and conductivity with respect to temperature, respectively. The resulting motion of the buffer and subsequent temperature and electric field distribution can be computed by solving conservation equations for mass and momentum (Navier-Stokes Equations), and thermal and electrical energy of the buffer solution (Ronald F. Probstein (1994) *Physicochemical Hydrodynamics, An Introduction*, Second Edition, John Wiley & Sons, Inc., New York, N.Y., incorporated herein by reference).

This body force will contribute to the fluid motion governed by the Navier-Stokes equations:

$$\rho_m\left[\frac{\partial\vec{u}}{\partial t} + (\vec{u}\cdot\nabla)\vec{u}\right] = -\nabla p + \mu\nabla^2\vec{u} + \vec{f},\ \nabla\cdot\vec{u} = 0$$

The thermal field is governed by the convection-diffusion equation:

$$p_m c_p\frac{\partial T}{\partial t} + \rho_m c_p(u\cdot\nabla)T = k\nabla^2 T + \sigma E^2$$

From the governing equations (Probstein, 1994) for fluid flow, electric field, and heat transfer, it can be seen that control of electrothermal flow in microfluidic systems will depend at least on:

Thermal properties (heat capacity, thermal conductivity) of the buffer solution as well as those of the material of the microdevice (such as glass, plastic, silicon, etc.);

Dielectric properties (permittivity, electric conductivity) of the buffer solution as well as their variation on temperature change;

The magnitude, frequency and waveform of the applied electric field;

Hydrodynamic properties (density and viscosity) of the buffer solution; and

Geometry of the flow region as well as electrode configuration.

Successful utilization of electrothermal effects to regulate flow within a microfluidic system relies on a correct choice of one or more of these parameters. For most applications, the thermal properties of the buffer solution are very close to those of water. The metal electrodes exhibit a much higher thermal conductivity as compared to glass, plastics or silicon, which are the materials most widely used in fabricating microdevices. Thus, thermal transfer within these materials can be discounted so that the materials are treated as being thermally insulated. Once the thermal parameters are chosen, the temperature change in the buffer solution will be determined primarily by the applied electric field. In microsystems for biological applications, the temperature change should often be maintained within a certain range, typically less than two degrees. Because the typical geometry for which electrothermal flow is most effective involves dimensions measured from tens of microns to hundreds of microns (this also being the range for electrode dimensions), the applied electric potential should range from a few volts to tens of volts.

The dielectric properties of the buffer solution are fixed in most applications, although in some cases a specific material (such as an electrolyte) is added to modify the electrical conductivity. The variations in conductivity and permittivity as a function of temperature ($\alpha$, $\beta$) can be found in the literature for most standard buffer solutions. For materials other than water, these two parameters may be different and must be determined by experimental measurement. The hydrodynamic properties of the buffer, such as the viscosity, are also fixed for a known buffer solution.

The applied electric field can be one of the following:

1. a direct current (DC) characterized by the magnitude of applied voltage;
2. a time varying direct current characterized by the magnitude and frequency of the applied voltage, and a having a waveform that can be sinusoidal, square, pulse, saw-toothed, or combination thereof; or
3. an alternating current (AC) characterized by magnitude and frequency of applied voltage and a waveform that can be sinusoidal, square, pulse, saw-toothed or combination thereof.

From the expression of the electrothermal force applied to the buffer solution, the force changes sign, in the case of an AC applied electric field, as the frequency increases from zero to infinity. For most applications, the critical frequency, where the force changes direction, is in the order of megahertz and the transition band is quite sharp. Therefore, the frequency of the AC field can be in the kilohertz to gigahertz range, depending on what is needed to control the flow.

System Design

When applying electrothermal flow to facilitate mixing and cleaning, the physics of the flow for a basic electrode structure should be understood. Because of the complex interactions among the electric, thermal and flow fields, it is only possible to solve analytically the electrothermally induced flow in a simple electrode configuration. An exact solution of electrothermal flow in the vicinity of a pair of elongated electrodes (kept along the surfaces of a wedge), which are separated by a gap of the same width as the electrode, can be straightforwardly constructed. The flow field is fundamentally characterized by a pair of oppositely circulating zones above each of the electrodes. The direction of circulation direction depends on the direction of the electrothermal force. The easiest way to control the flow direction is to change the AC field frequency. Depending on the frequency, the flow can move toward or away from the center of the electrode. Because of the incompressibility of the flow, the fluid is expelled away or pulled toward the gap between the electrodes. The size of the circulation zone is approximately the same order of the size of the electrode. It is anticipated that the flow structure shares a similar topology for a pair of electrodes fabricated on each of the surfaces of a wedge region. For an array of periodical, co-planar electrode strips, the electrothermal flow is characterized by an array of circulating zones above each electrode. The direction of the flow is reversed for adjacent electrodes. The circulating zones are squeezed along the electrodes and therefore, they stretch in other directions. In general, the circulating zones are of comparable size to the electrode dimensions.

Although the local electrothermal force increases as the electrode gap decreases, the circulating zones are localized near the tips of the electrodes. This tends to work against a thorough mixing of fluid that is separated from the electrodes. In practice, however, the dimensions and the gap of the electrodes should be comparable with the other dimensions of the channel.

Figure 11:
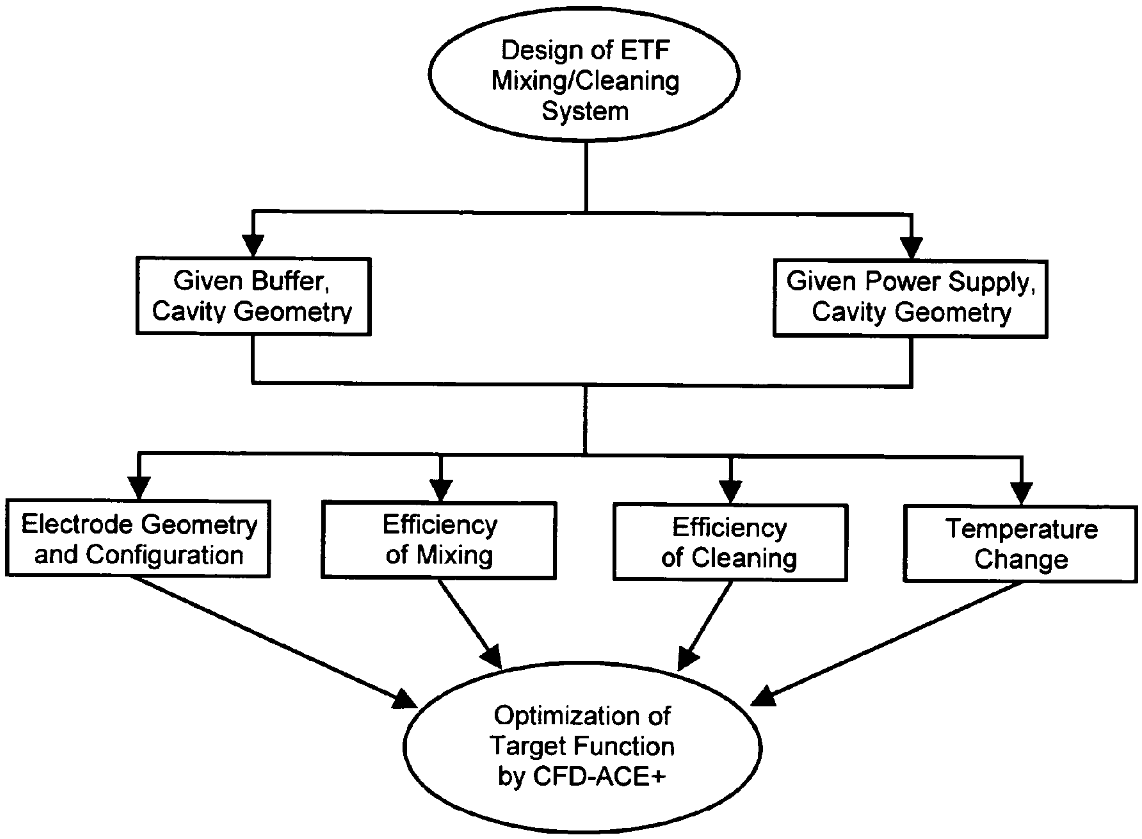
FIG. 11 is a flow chart showing one embodiment of a method of designing a microfluidic system that uses electrothermal flow for cleaning/mixing within cavities or channels in the system.

In general, issues that must be addressed for a successful design of a mixing or cleaning microfluidic system using electrothermal flow are summarized in the diagram shown in FIG. 11. The design of a mixing or cleaning system can be divided into two major categories: one based on a fixed buffer solution and another based on a fixed electric power source. Thus, an initial determination is whether the design is constrained by use of a specific buffer solution and channel geometry, or by use of a specific power source and channel geometry. Next, a key element of the design is the appropriate choice of electrode configuration, as well as correct values for adjustable parameters in order to achieve optimized performance of either a mixing or cleaning system. For design purposes in each category, it is assumed that the dimensions of the cavity are fixed. Accordingly, the adjustable parameters will be the magnitude of the voltage applied to the electrodes, the frequency of the applied voltage, the voltage waveform, and/or the dielectric properties of the buffer. A change of conductivity can be achieved by adding electrolyte to the buffer. A change in frequency of the field will alter the flow direction. In all applications, the temperature change in the buffer should be minimized so that the biological samples will not be damaged. The efficiency of mixing or cleaning should be as high as possible.

All of these factors form a complicated optimization problem with certain restrictions. Accordingly, a preferred embodiment of the invention includes simulation of the proposed system using computational fluid dynamics (CFD) techniques and tools. For example, CFD-ACE+® (ESI Group) multiphysics software developed and marketed by CFD Research Corporation, Huntsville, Ala., and its capability of optimization, can be used to determine the most suitable parameters. The CFD-ACE+® software modules of particular relevance to the present invention are fluid flow, heat transfer, multiple species transport, bio- and electro-chemistry, particle transport, and electrostatics.

Simulation-based process and device design is a rapidly emerging paradigm shift in the biotechnology and medical device industries. This design method relies on solving the laws of underlying complex, interacting, physico-chemical phenomena, and creating "virtual" device/process models. Compared to traditional empirical and laboratory analysis, this method provides a fundamental and detailed understanding of the device or process performance. A typical simulation-based design and optimization process for purposes of designing a microfluidic device using electrothermal flow consists of three basic steps:

(1) The designer creates a geometric representation of the system. The device is sub-divided into discrete non-overlapping three-dimensional cell volumes with the help of a computational mesh using a geometric grid generation tool.

(2) The governing system of nonlinear partial differential equations that describe fluid flow, heat transfer, multiple species transport, bio- and electro-chemistry, particle transport and electrostatics is solved. Simulations are performed for the prescribed values of process conditions such as magnitude, frequency and waveform of the applied electric field, buffer and analyte flow rates, and physical and chemical properties of the buffer and the analyte. In addition to these, the orientation and the number of electrodes can also be varied, and their implications on system performance can be analyzed.

(3) Finally, the performance of the device is analyzed using the post-processing tool.

If the performance of the system is found to be unsatisfactory, the designer will change either the process conditions and repeat steps 2 and 3, or will change the system geometry and repeat steps 1 through 3, until optimal (desired) performance is achieved. Steps 1 through 3 will be repeated if the number and orientation of the electrodes are changed.

Examples are provided below for design of mixing and cleaning systems using CFD design and simulation techniques in accordance with the invention. A 100 kHz AC electric field is used for each simulation.

Mixing

Figure 7:
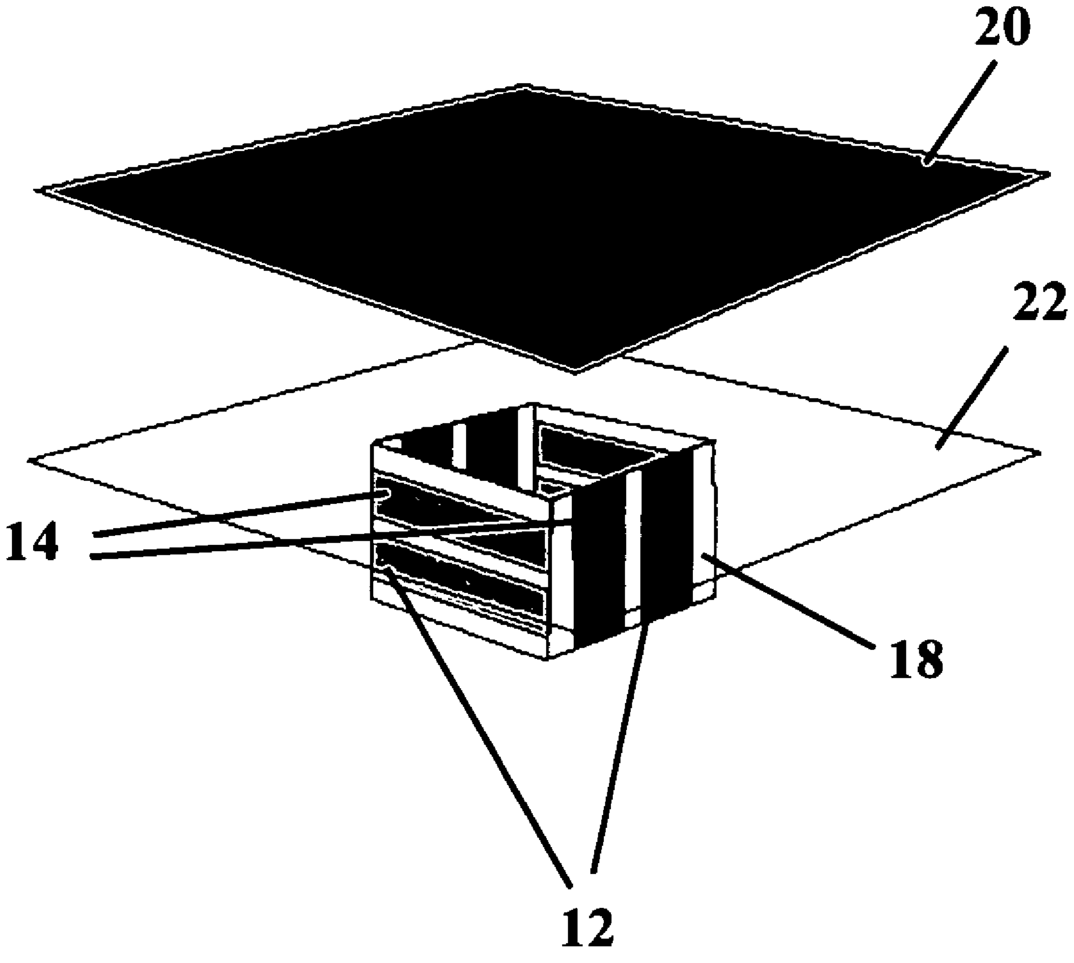
FIG. 7 is an oblique cutaway view of a rectangular cavity in a microfluidic system with multiple electrode pairs arranged on the cavity walls to electrothermally induce mixing of liquids in the cavity.
Figure 8:
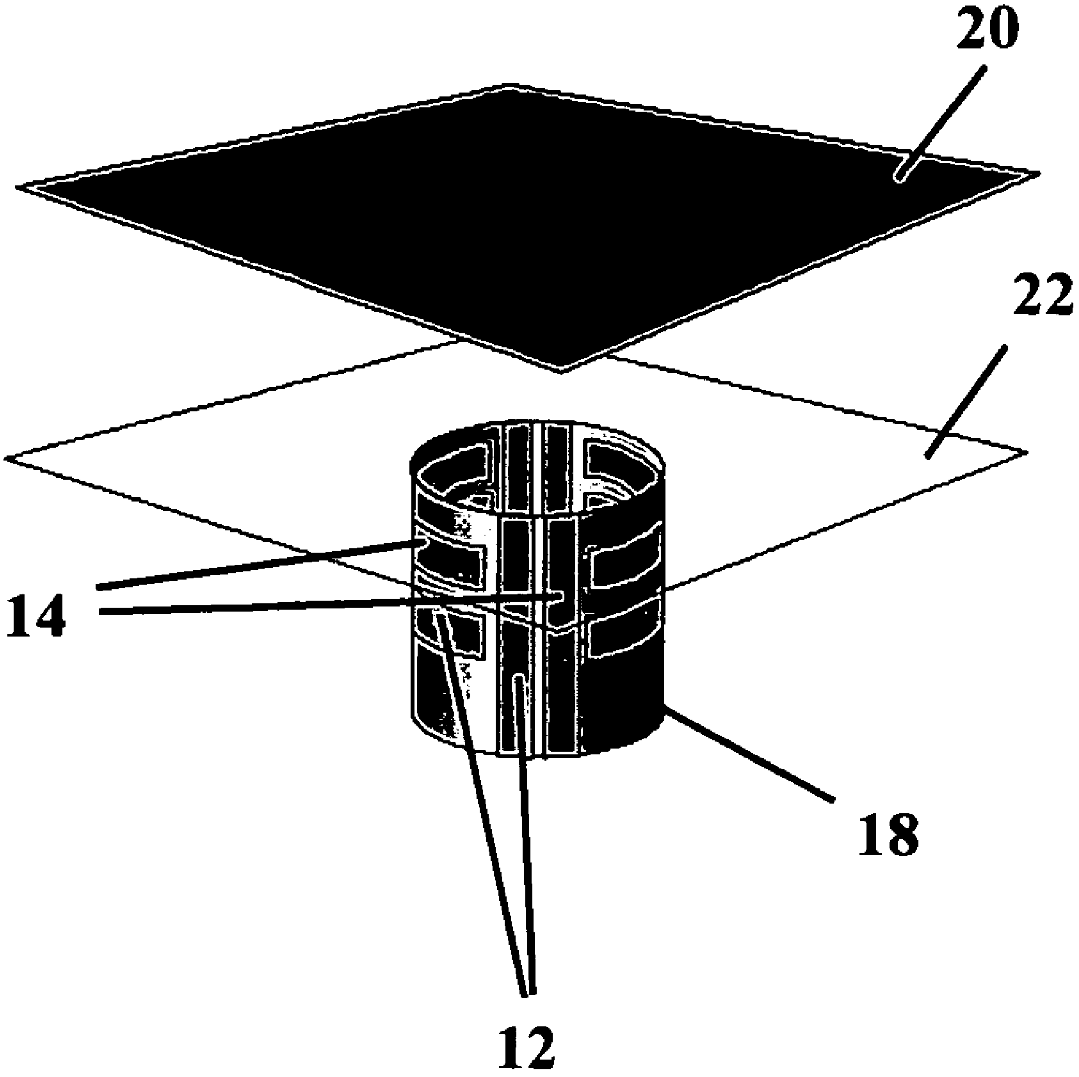
FIG. 8 is an oblique cutaway view of a cylindrical cavity in a microfluidic system with multiple electrode pairs arranged on the cavity wall to electrothermally induce mixing of liquids in the cavity.

A rectangular cavity 18 is shown in FIG. 7 positioned proximate an upper substrate 20 and lower substrate 22 in a microfluidic system. Multiple electrode pairs 12, 14 are fabricated on each surface of the cavity 18. In the embodiment shown in FIG. 7, the electrode pairs 12, 14 on two of the opposed side walls of the cavity 18 are oriented vertically. The electrode pairs 12, 14 on the other opposed side walls of the cavity 18 are oriented horizontally. In FIG. 8, a cylindrical cavity 18 is shown, with multiple electrode pairs 12, 14 oriented both vertically and horizontally on the cylinder wall.

The electrode pairs 12, 14 are electrically connected to an AC voltage source (not shown) that generates a voltage having a magnitude and frequency that are selectable/controllable by the designer/user in order to provide the desired flow motion control in accordance with the design criteria as described herein. In either embodiment, in order to provide the desired flow control, the electrode pairs 12, 14 can be energized by the AC voltage source to work simultaneously, or they can be activated periodically.

In one embodiment, two buffer solution species SPA (1 nM) and SPB (3 nM) occupy the top and bottom half of a 200 micron×100 micron rectangular cavity. The solutions have diffusivities of 1 and 3 E-10 $m^2/s$, respectively. An AC voltage of 5 Vrms is applied to the electrodes. Model parameters are:

$$\epsilon_r=80,\ \sigma=560\ \mu S/cm,\ k=0.6\ W/m\ K,\ C_p=4180\ J/Kg\ K$$

Figure 3:
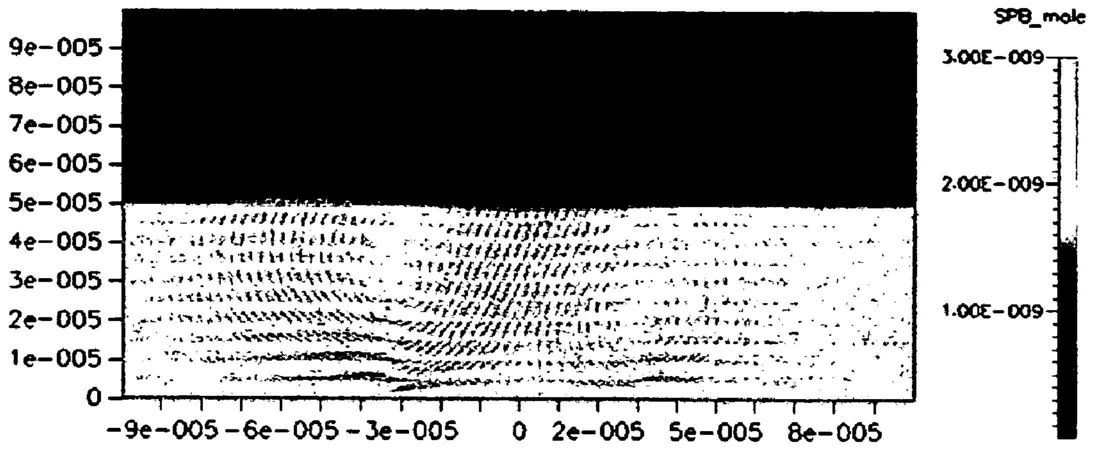
FIGS. 3(*a*) and 3(*b*) are contour plots of SPA species concentration at t=0.025, using a micromixing simulation model in accordance with the invention, wherein two buffer solution species SPA (1 nM) and SPB (3 nM) occupy the top and bottom half of a 200 micron×100 micron rectangular cavity. The solutions have diffusivities of 1 and 3 E-10 $m^2/s$, respectively. A voltage of 5 Vrms is applied to the electrodes.
Figure 3:
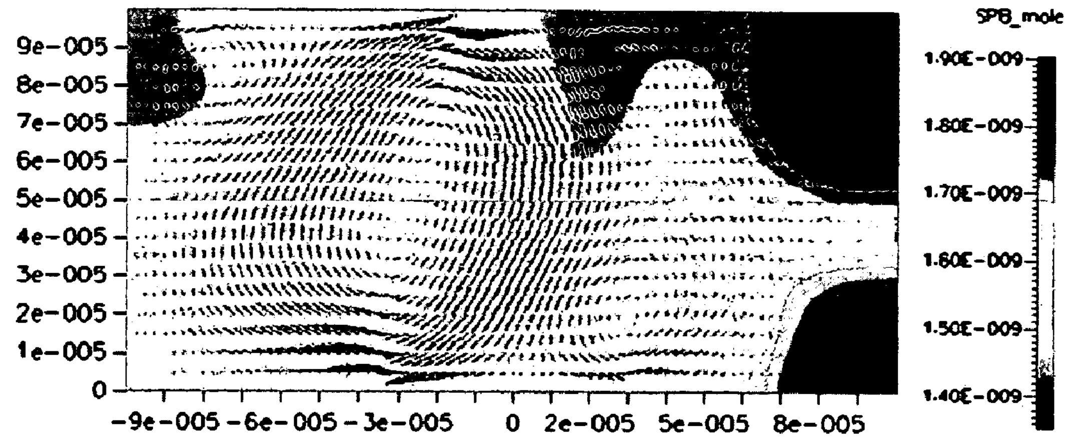

The resulting flow field is shown in FIG. 3, with a maximum induced velocity of 200 microns/sec due to electrothermal effects. The contour plot of species concentration for SPA is also shown at t=0.025 in FIG. 3(*a*) and 5 s in FIG. 3(*b*).

Figure 15:
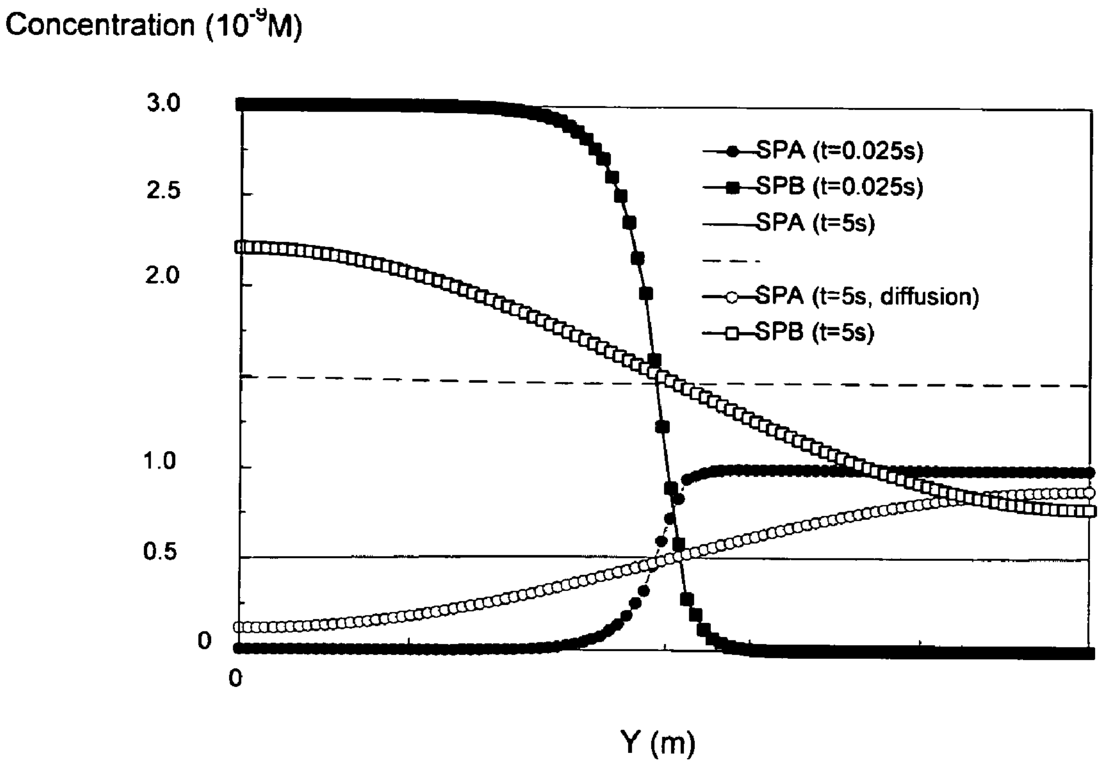
FIG. 15 shows simulation results for mixing with and without electrothermal flow.

A concentration profile along the vertical axis at the center of the device is shown for both species SPA and SPB in FIG. 15. A detailed analysis of this case study clearly indicates that 97% of mixing can be accomplished in less than 2 seconds. If the mixing were allowed to happen by pure diffusion, it would have taken more than 10 seconds to achieve this level (97%) of mixing.

Figure 14:
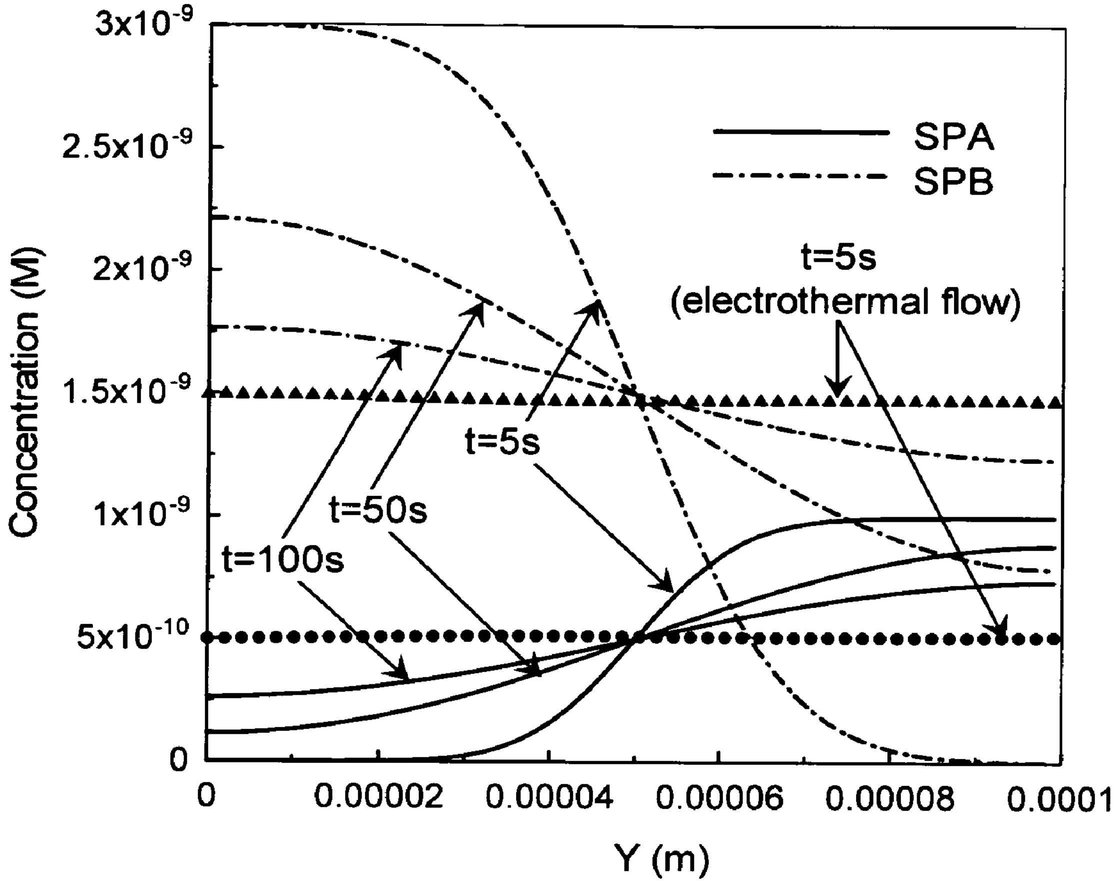
FIG. 14 shows the results of a mixing simulation and enhanced mixing with electrothermal flow.

Note that the diffusion coefficients used for both species would classify them as small molecules. For macromolecules, such as proteins, the diffusion coefficient is expected to be at least an order of magnitude smaller, which would make the present invention even more effective (i.e. mixing time reduced by more than two orders of magnitude). Such results are presented in FIG. 14 above whereby mixing that is faster by an order of magnitude is achieved by electrothermally induced flow.

Figure 4:
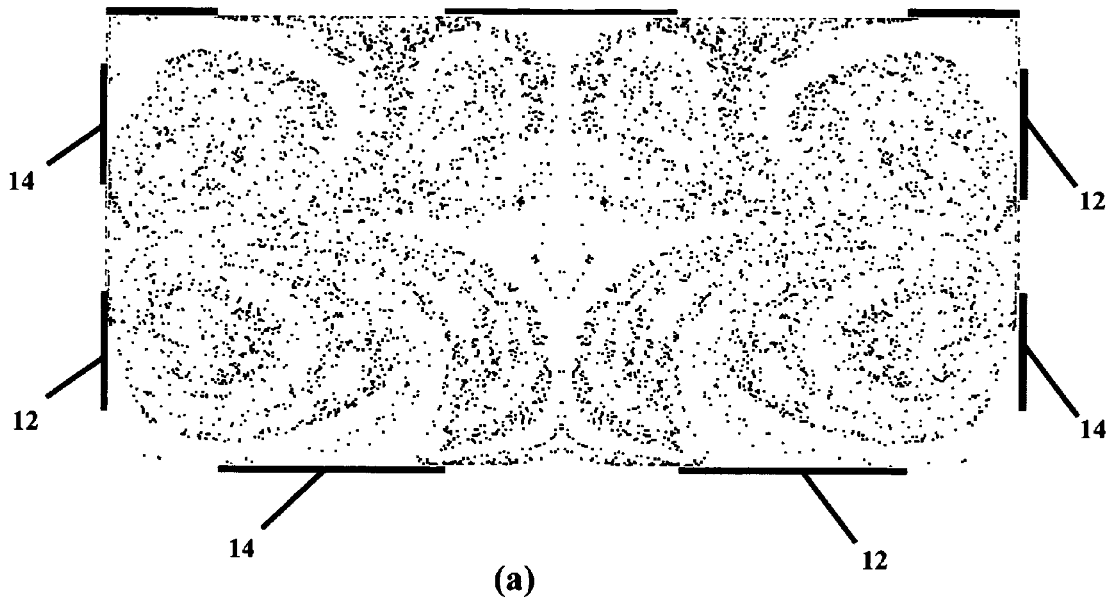
FIGS. 4(*a*) and 4(*b*) illustrate a tracer configuration in a simulation model of an electrothermal mixing system, before and after mixing occurs.
Figure 4:
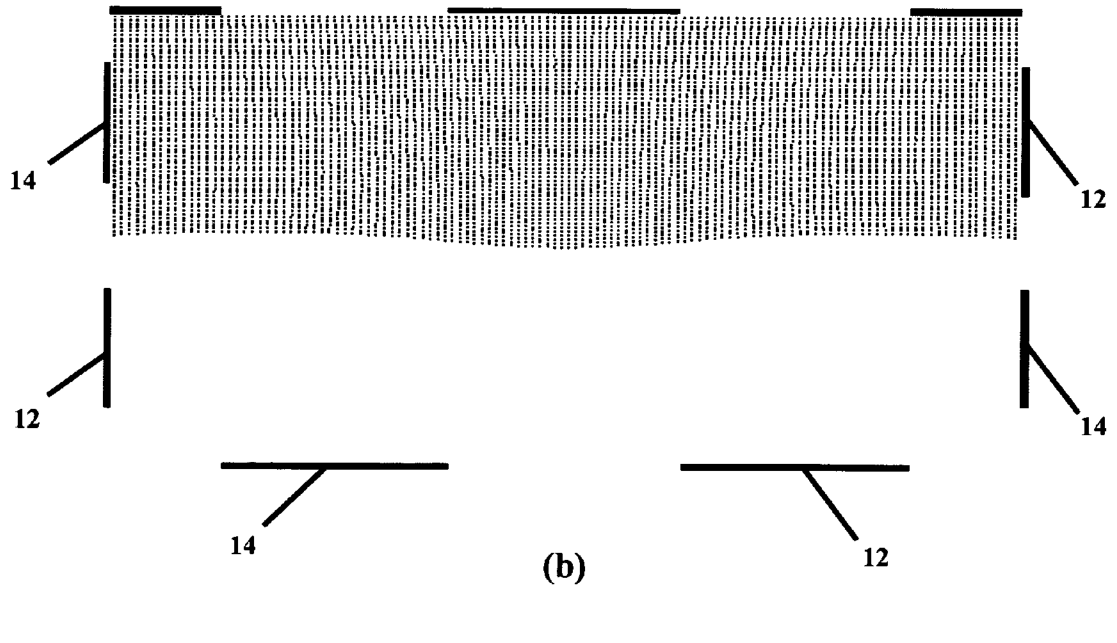
Figure 12:
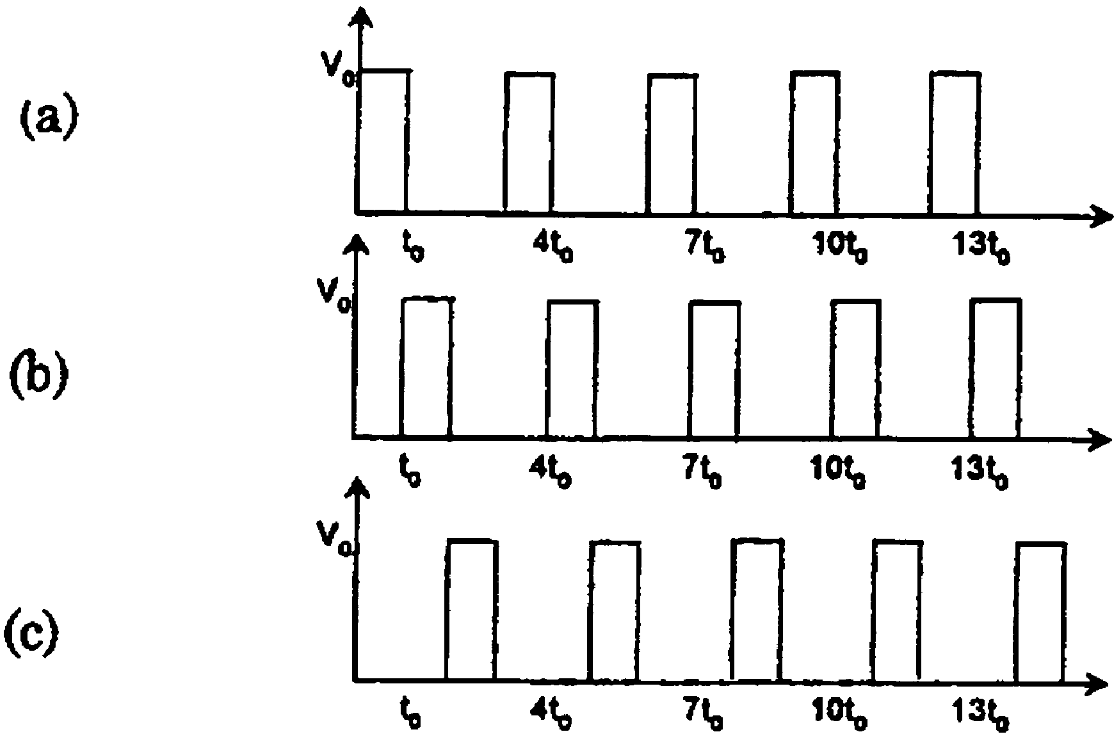
FIGS. 12(*a*)-(*c*) are timing diagrams showing the voltage applied to the electrodes on the lower (FIG. 12(*a*)), top (FIG. 12(*b*)) and side walls (FIG. 12(*c*)) for electrothermally inducing mixing in a rectangular cavity.

As a further example, the electrode configuration in a rectangular cavity as shown in FIG. 7 produces more effective mixing. FIG. 12 shows the voltage applied to the electrodes on the lower, top, and side walls, FIGS. 12(*a-c*), of the cavity, which varies periodically with a periodicity of 3 $t_0$. In this embodiment, as shown by the timing of the applied voltages in FIG. 12, the electric fields are sequentially generated at the cavity surfaces. Thus, the fields generated at these electrodes will stretch and fold the fluid within the cavity and the boundary of tracers which initially occupy the upper half of the cavity increases exponentially, which is strong evidence of chaotic flow. FIG. 4(*a*) shows the tracer configuration before mixing and FIG. 4(*b*) illustrates the tracer configuration relative to electrode pairs 12, 14 after only two periods. In this embodiment, the cavity dimensions are 200 microns×400 microns, and $t_0$=2 s. Other parameters are the same as described above.

Figure 6:
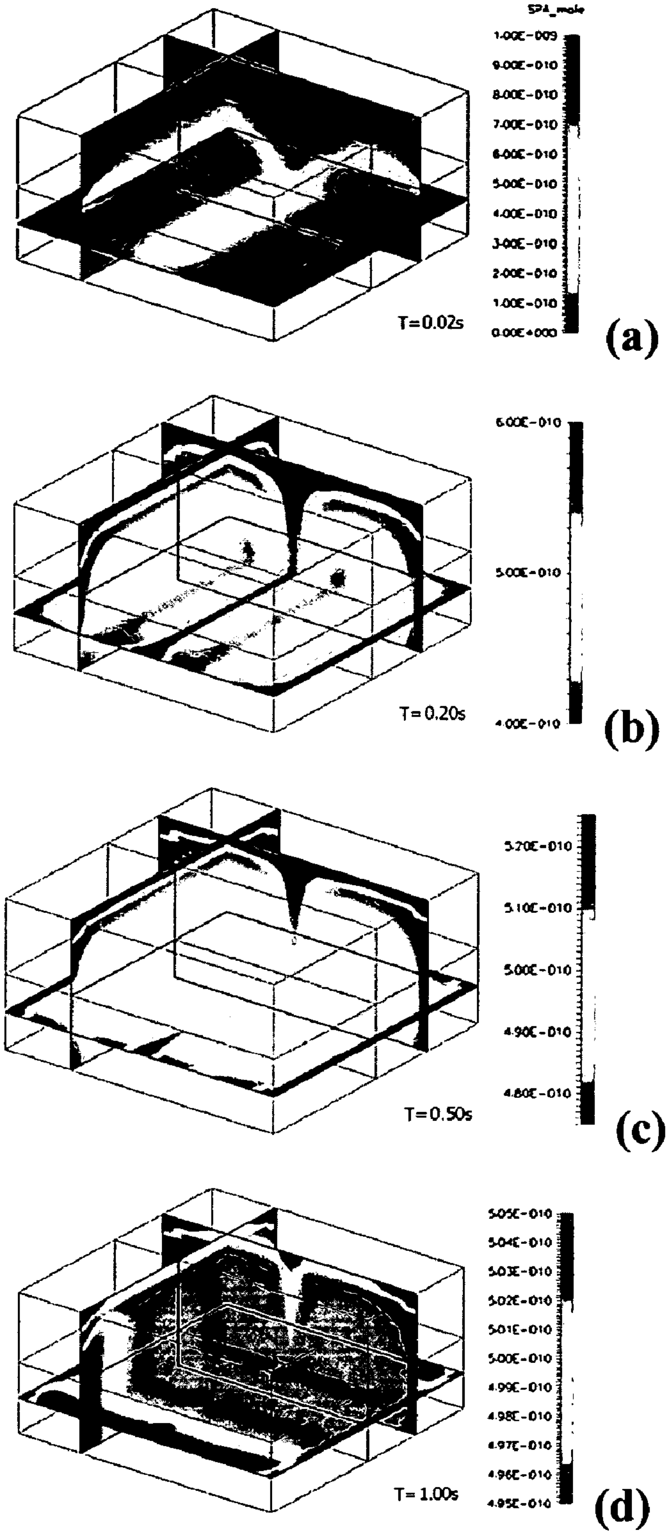
FIGS. 6(*a*)-(*d*) graphically illustrate a three-dimensional simulation of mixing of two species in a microfluidic system in accordance with the present invention. The two species, SPA (C=1 nM, D=$2\times10^{-12}$ $m^2/s$) and SPB (C=3 nM, D=$4\times10^{-12}$ $m^2/s$), initially occupy the upper and lower half of a rectangular cavity of size 40 microns×40 microns×20 microns. A pair of electrodes is symmetrically placed on the bottom of the cavity. The electrode width is 10 mm. An AC electric field having a nominal frequency of $10^5$ Hz is applied. The peak voltage applied to the electrodes is ±5 V.

FIG. 6 illustrates a three-dimensional simulation of mixing of two species in a microfluidic system. The two species, SPA (C=1 nM, D=$2\times10^{-12}$ $m^2/s$) and SPB (C=3 nM, D=$4\times10^{-12}$ $m^2/s$) initially occupy the upper and lower half of a rectangular cavity of size 40 microns×40 microns×20 microns. A pair of electrodes is symmetrically placed on the bottom of the cavity. The electrode width is 10 mm. An AC electric field of $10^5$ Hz is applied. The peak voltage is ±5V. This field will create a strong electrothermally induced flow with a maximum velocity of approximately 0.7 mm/s. The instantaneous concentration of species A is shown in FIG. 6(*a-d*) for T=0.02 s, 0.20 s, 0.5 s, and 1.0 s, after the electric field is applied. The mixing is excellent and fast in the wide portion of the cavity, except at the corners and in the region close to the cavity walls, where convection is minimum. In practice, more electrodes can be placed on the sidewalls of the cavity to assist mixing in other directions.

In order to achieve optimal mixing while maintaining the temperature change within a certain range, the position of the electrodes on each surface of the cavity should be adjusted. To do this, the designer should define a target function that comprises temperature increase and the uniformity of the concentration. The position of the electrodes will be adjusted based on performing an optimization procedure of this target function. For example, the CFD-ACE+® (ESI Group) software provides automatic implementation of the whole process.

Cleaning

Conventional methods of washing microcavities in a channel do not achieve good cleaning efficiency because of the closed circulation of the fluid in the channel. The conventional method to enhance cleaning is to use a time-dependent washing process which attempts to create chaotic flow. Electrothermal induced flow provides an effective way to achieve this objective. By placing one electrode in the channel and another outside but near the channel, a flow is induced which moves locally parallel to the side walls of the channel. This in turn carries along with it any analyte or sample trapped inside the channel, to a location above the opening of the channel, where washing flow will remove them. By repeating this process, i.e., turning the electrothermal flow on and off, the channel can be cleaned. Flow direction may also be repeatedly reversed to enhance cleaning. This cleaning process is also applicable to other biochip components, such as pumps and sensors, as well as junctions connecting these components.

Figure 9:
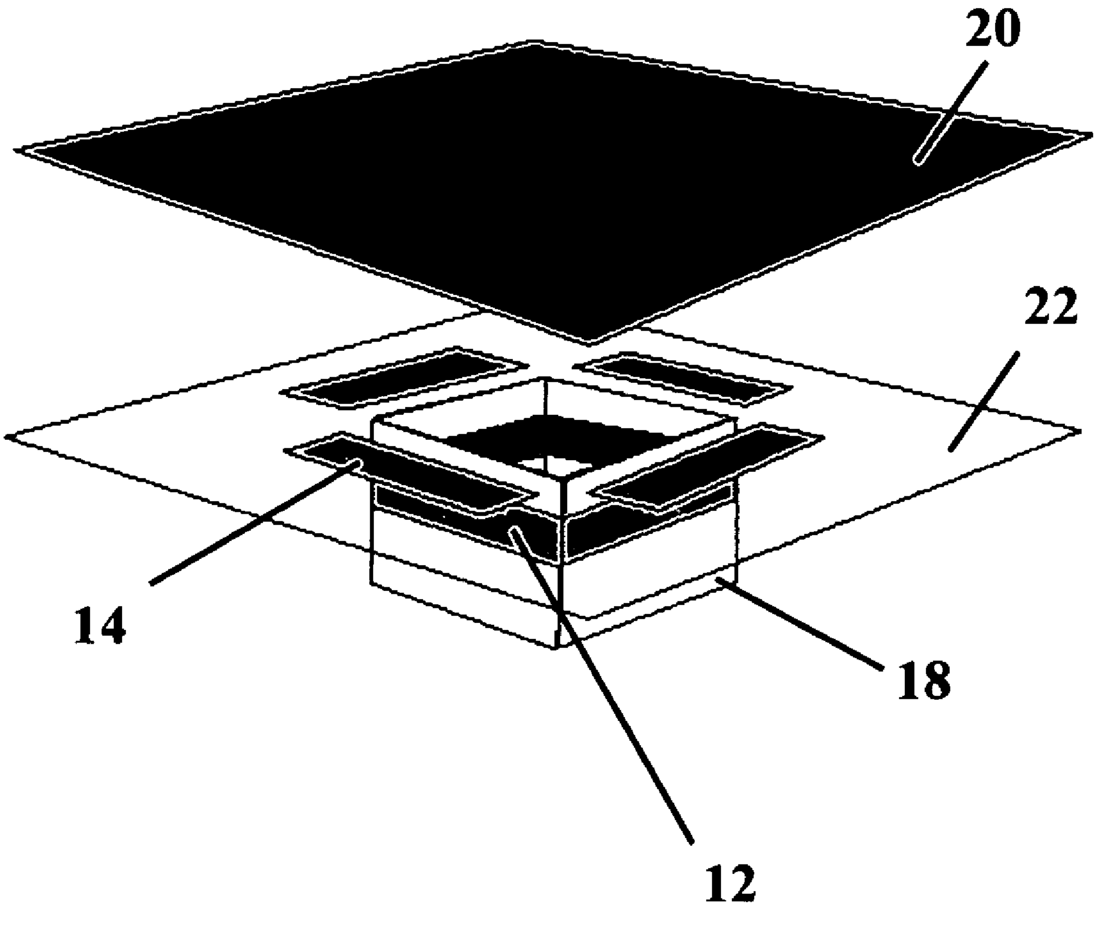
FIG. 9 is an oblique cutaway view of a rectangular cavity in a microfluidic system with multiple electrode pairs arranged on the cavity walls and outside the cavity to electrothermally induce cleaning of the cavity.
Figure 10:
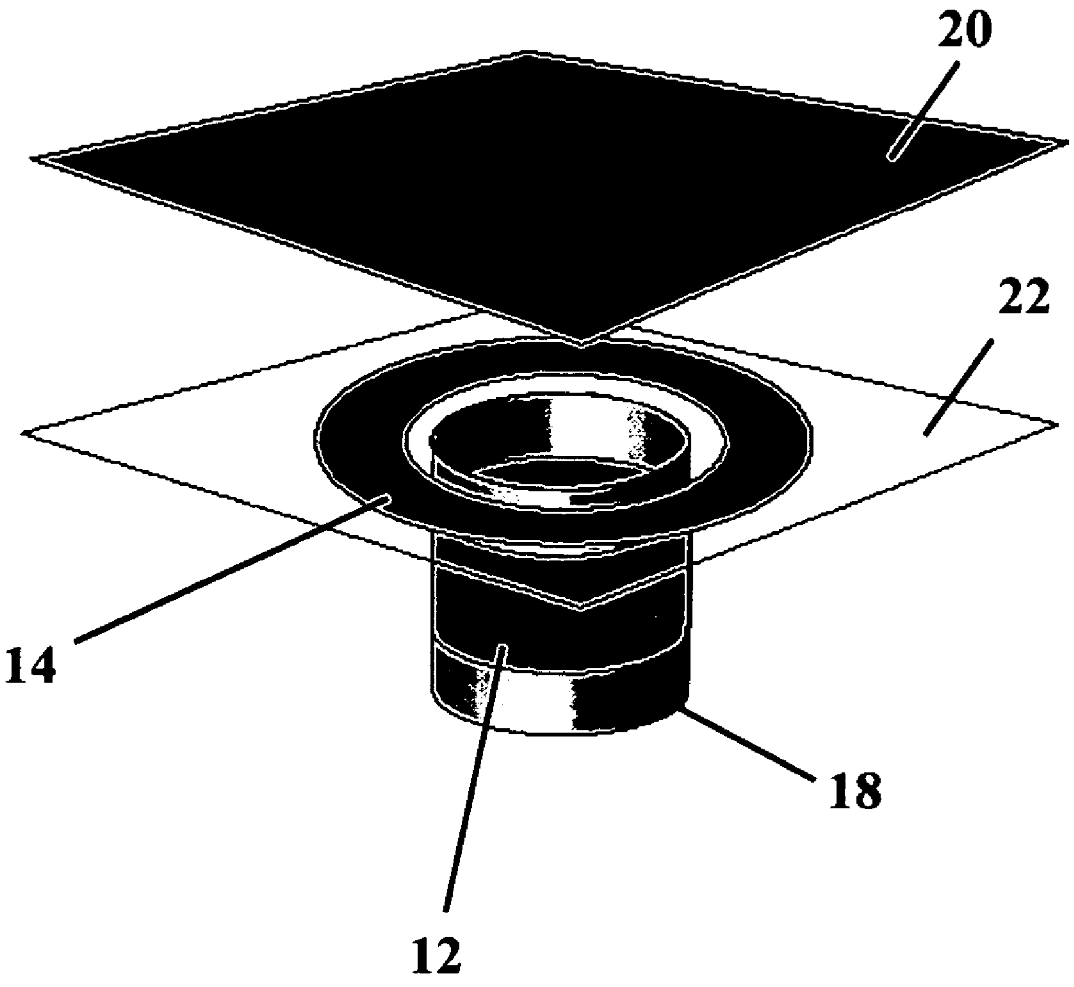
FIG. 10 is an oblique cutaway view of a cylindrical cavity in a microfluidic system with an electrode pair arranged on and proximate to the cavity wall to electrothermally induce cleaning in the cavity.
Figure 13:
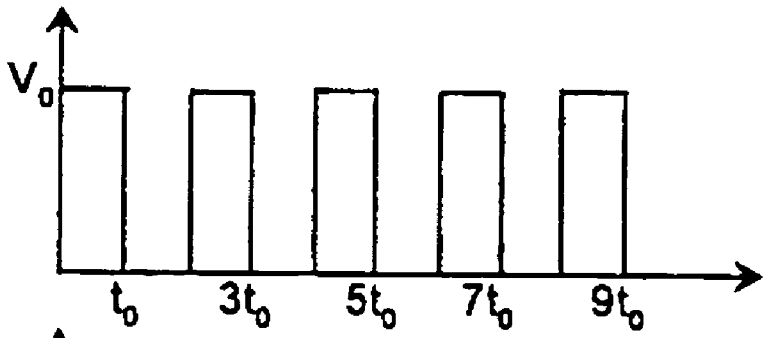
FIGS. 13(*a*) and 13(*b*) show a timing diagram for the voltage applied to an electrode pair for a cylindrical cavity to cause electrothermally inducing cleaning within the cavity and the resulting washing velocity over time.
Figure 13:
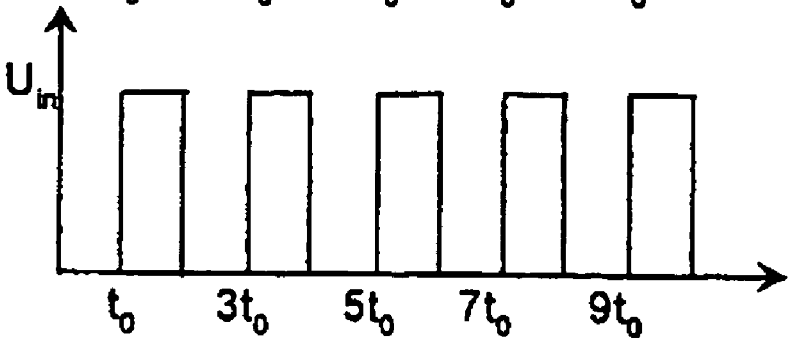

FIG. 9 illustrates one configuration of multiple electrode pairs 12, 14 positioned with respect to a rectangular cavity 18 proximate an upper substrate 20 and lower substrate 22 in a microfluidic system or array. The first electrode 12 of each electrode pair is positioned on or in the side wall of the cavity 18. The second electrode 14 of each electrode pair is positioned proximate to the cavity opening outside the cavity. Each pair of electrodes 12, 14 is electrically connected to an AC voltage source (not shown) to induce electrothermal flow for purposes of cleaning the cavity 18. FIG. 10 shows an alternative electrode configuration for use with a cylindrical cavity 18. FIG. 13(*a*) shows the applied voltage and FIG. 13(*b*) shows the resulting washing velocity over time in one embodiment of a cleaning system in accordance with the invention.

Figure 5:
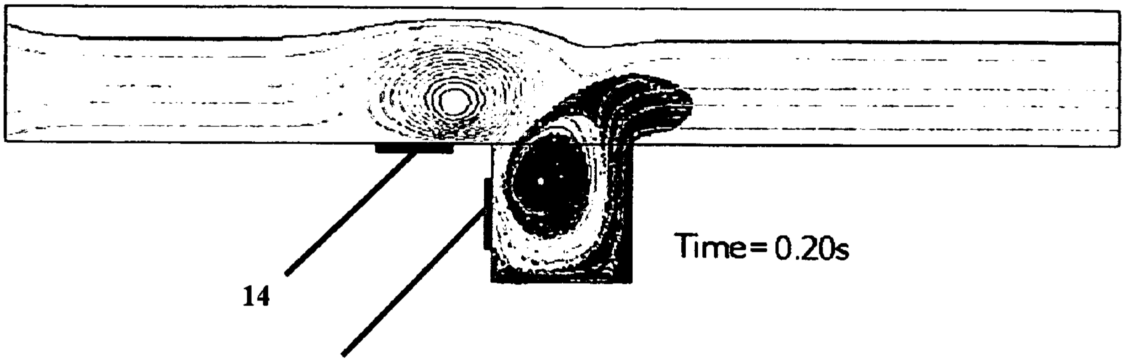
FIGS. 5(*a*) and 5(*b*) graphically illustrate simulation of electrothermally induced flow patterns in a microfluidic cleaning application in accordance with the present invention, with two electrodes having a width of 10 microns positioned 5 microns from the corner of the cavity and with a 5 V AC field applied. The results are shown for 10,000 particles at t=0.2 (FIG. 5(*a*)) and t=0.4 s (FIG. 5(*b*)).
Figure 5:
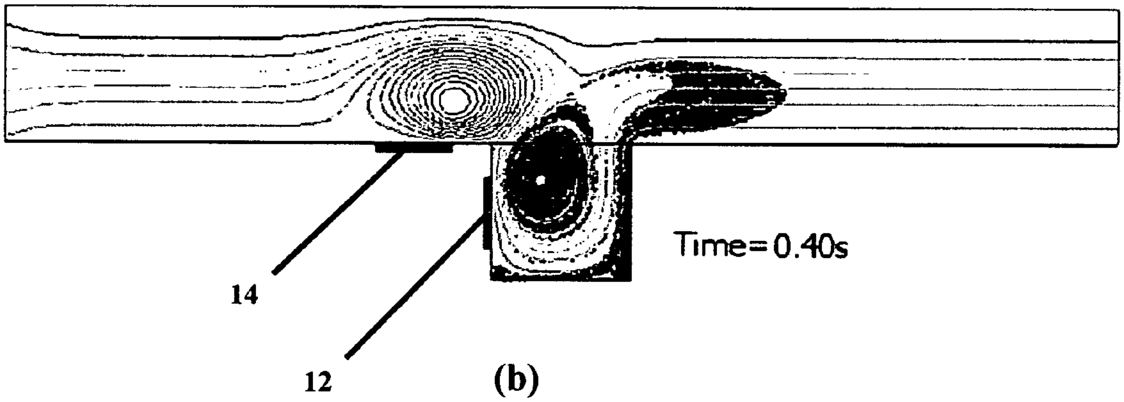

Removal of sub-micron/nano-particles trapped in a channel can be substantially enhanced by combining electrothermally induced flow with pressure-driven flows. To design and implement such a system, a simulation is performed for 20 nm particles initially uniformly distributed in a 20 micron×20 micron cavity along the lower channel wall. Such particle sizes and cavity dimensions are representative of those that exist in typical microfluidic systems. Two electrodes, 12 and 14 having a width of 10 microns are positioned 5 microns from the corner of the cavity and a 5 Vrms AC field is applied. The electrothermally induced flow creates a circulatory flow pattern within the cavity that levitates the particles. A parabolic flow in the channel is used to wash away the levitated particles. The results are shown in FIG. 5 for 10,000 particles configuration at t=0.2 (FIG. 5(*a*)) and t=0.4 s (FIG. 5(*b*)). The electrothermally induced flow can be applied in a periodic manner in order to achieve a higher particle removal rate.

Figure 16:
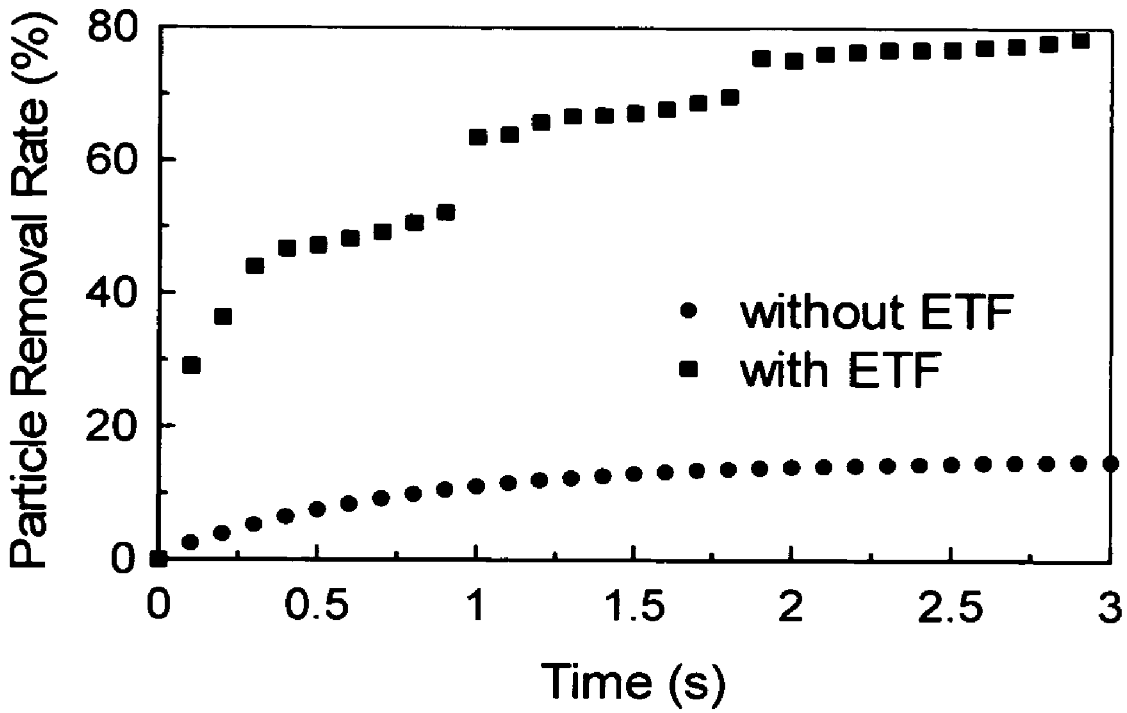
FIG. 16 shows the simulated particle removal rate during the cleaning of a microfluidic device with and without electrothermal flow.

FIG. 16 shows the particle removal rate for periodic electrothermally induced flow with a time period of 0.5 seconds. The particle removal rate is increased by 65% after 3 seconds compared to the case with only pressure driven flow. By properly arranging and optimizing the electrode configuration and operating conditions, it is possible to achieve more thorough cleaning of the cavity in a short time.

Electrode Configuration and Fabrication

Figure 2:
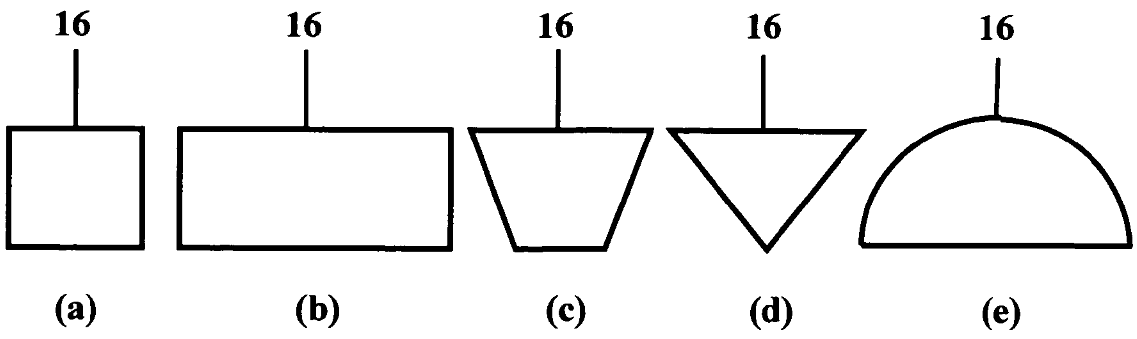
FIGS. 2(*a*)-(*e*) are end views of different microfluidic channels in which electrodes can be used to electrothermally induce flow motion.

At least one pair of electrodes 12, 14 (two discrete planar or curved) is needed to generate the electrothermally induced flow. These electrodes 12, 14 can be oriented in-plane or out of plane (0<=θ<=360 degrees) as shown in FIG. 1. Also, the electrodes can be placed opposite or adjacent each other inside the microchannel or microfluidic device. As shown in FIG. 2, the cross-sectional geometry of the microchannels 16 can be square as shown in FIG. 2(*a*), rectangular as shown in FIG. 2(*b*), trapezoidal as shown in FIG. 2(*c*), triangular as shown in FIG. 2(*d*), or semicircular as shown in FIG. 2(*e*).

Two basic electrode configurations can be used in simulations and in physical implementation of systems in accordance with the invention: (i) a pair of inline electrodes (along the surface of the microchannel); and (ii) a pair of electrodes placed on each surface of a wedge region. Analytic study of electrothermal flow in a wedge region due to a pair of in-plane electrodes on each surface, forming an angle of θ (see FIG. 1), shows that a pair of circulation zones is generated, in which the fluid is pulled toward the vertex of the wedge or otherwise depending on the properties of the fluid as well as frequency of the applied electric field. The induced flow will enable sample mixing or cleaning.

Methods for fabrication of microelectrodes on substrates are known. The most common method is photolithography, which is well established in the semiconductor industry, as taught in Wang et al. (2000) "Cell separation by dielectrophoretic field-flow-fractionation" *Anal. Chem.* 72: 832-839, which is incorporated herein by reference. Using this method, others have used microelectrode arrays to separate biological cells using dielectrophoresis (M. Hughes & H. Morgan (1999) "Dielectrophoretic characterization and separation of antibody-coated submicrometer latex sphere" *Anal. Chem.* 71:3441-3445). A variation of this technique is direct-write electron beam lithography. Both methods are capable of fabricating multiple layers of metals on glass substrate. A sophisticated procedure has been developed, which combines laser ablation and photolithography to construct three dimensional microelectrodes on a glass substrate (Muller et al. (1999) "A 3-D microelectrode system for handling and caging single cells and particles" *Biosensors & Bioelectronics* 14:247-256).

The simulation-based design and optimization process using CFD-ACE+ software, for example, described in the previous section, will also be useful in the investigation and development of various devices/concepts using electrothermally induced flow phenomena. The methods and the systems that are described in the present invention related to sample mixing and cleaning in Microsystems can be readily applied in other applications such as micropumps, microreactors, microjets, active valves and particle/cell sorting and counting. These devices find applications in the BioMEMS/biotechnology industry in the field of proteomics, genomics, diagnostics and high-density chemical analysis applications, and in polymerase chain reaction (PCR) chips.

Thus, although there have been described particular embodiments of the present invention of new and useful Methods and Systems Employing Electrothermally Induced Flow for Mixing and Cleaning in Microsystems, it is not intended that such references be construed as limitations upon the scope of this invention except as set forth in the following claims.

What is claimed is:

1. A mixing element for a microdevice comprising:

a) a mixing compartment having a principal axis of symmetry in fluid communication with a channel and b) first through fourth pairs of electrically coupled, elongated mixing electrodes located on the interior surface of the mixing compartment wherein:

(i) the first electrodes of the first and second mixing electrode pairs are adjacent and parallel to one another and aligned axially with respect to the principal axis of symmetry;

(ii) the second electrodes of the first and second mixing electrode pairs are adjacent and parallel to one another and aligned with a plane orthogonal to the principal axis of symmetry;

(iii) the first electrodes of the third and fourth mixing electrode pairs are adjacent and parallel to one another and aligned axially with respect to the principal axis of symmetry; and (iv) the second electrodes of the third and fourth mixing electrode pairs are adjacent and parallel to one another and aligned with a plane orthogonal to the principal axis of symmetry.

2. The mixing element of claim 1, wherein the mixing compartment has a square or rectangular cross sectional geometry.

3. The mixing element of claim 1 wherein the principal axis of symmetry is orthogonal to the channel.

* * * * *